(12) United States Patent
Baccelli

(10) Patent No.: US 10,182,846 B2
(45) Date of Patent: *Jan. 22, 2019

(54) SPINAL IMPLANT

(71) Applicant: Zimmer Spine S.A.S., Bordeaux (FR)

(72) Inventor: Christian Baccelli, Saucats (FR)

(73) Assignee: Zimmer Spine S.A.S., Bordeaux (FR)

( * ) Notice: Subject to any disclaimer, the term of this patent is extended or adjusted under 35 U.S.C. 154(b) by 132 days.

This patent is subject to a terminal disclaimer.

(21) Appl. No.: 14/534,327

(22) Filed: Nov. 6, 2014

(65) Prior Publication Data

US 2015/0066090 A1    Mar. 5, 2015

Related U.S. Application Data

(63) Continuation of application No. 13/040,404, filed on Mar. 4, 2011, now Pat. No. 8,882,808, which is a
(Continued)

(30) Foreign Application Priority Data

Sep. 4, 2003   (FR) ...................... 03 10480

(51) Int. Cl.
*A61B 17/70* (2006.01)

(52) U.S. Cl.
CPC ...... *A61B 17/7032* (2013.01); *A61B 17/7047* (2013.01); *A61B 17/7056* (2013.01)

(58) Field of Classification Search
CPC ............ A61B 17/7032; A61B 17/7047; A61B 17/7056
See application file for complete search history.

(56) References Cited

U.S. PATENT DOCUMENTS

| 255,428 A | 3/1882 | Graham |
| 4,946,458 A | 8/1990 | Harms et al. |
(Continued)

FOREIGN PATENT DOCUMENTS

| DE | 3032237 A1 | 3/1982 |
| DE | 3916198 A1 | 11/1990 |
(Continued)

OTHER PUBLICATIONS

"U.S. Appl. No. 10/569,607, Examiner Interview Summary dated Jul. 12, 2010", 4 pgs.
(Continued)

*Primary Examiner* — Samuel Hanna
(74) *Attorney, Agent, or Firm* — Schwegman Lundberg & Woessner, P.A.

(57) ABSTRACT

This disclosure relates to a spinal implant that can provisionally retain a rod in an assembly head without having to first lock the rod relative to the assembly head. The spinal implant has a clip insert structured to retain the rod in the assembly head. The clip insert has a top portion with a cylindrical opening and extending over the cylindrical opening to cover the connection rod in part when the connection rod is engaged in the clip insert. The top portion is deformable by application of force on the connection rod to engage the connection rod with the clip insert. The clip insert and the assembly head are mechanically decoupled and can be fully received within the assembly head. The mechanical forces to which the assembly head is subjected are not transmitted to the clip insert.

10 Claims, 3 Drawing Sheets

Related U.S. Application Data continuation of application No. 10/569,607, filed as application No. PCT/FR2004/002249 on Sep. 3, 2004, now Pat. No. 7,901,436.

(56) References Cited

U.S. PATENT DOCUMENTS

| | | |
|---|---|---|
| 4,950,269 A | 8/1990 | Gaines |
| 5,010,879 A | 4/1991 | Moriya et al. |
| 5,147,359 A | 9/1992 | Cozad et al. |
| 5,181,917 A | 1/1993 | Rogozinski |
| 5,201,734 A | 4/1993 | Cozad et al. |
| 5,207,678 A | 5/1993 | Harms et al. |
| 5,346,493 A | 9/1994 | Stahurski et al. |
| 5,380,324 A | 1/1995 | Muller |
| 5,385,583 A | 1/1995 | Cotrel et al. |
| 5,437,669 A | 8/1995 | Yuan et al. |
| 5,443,467 A | 8/1995 | Biedermann et al. |
| 5,536,268 A | 7/1996 | Griss et al. |
| 5,545,165 A | 8/1996 | Biedermann |
| 5,562,663 A | 10/1996 | Wisnewski et al. |
| 5,628,740 A | 5/1997 | Mullane et al. |
| 5,630,817 A | 5/1997 | Rokegem et al. |
| 5,672,176 A | 9/1997 | Biedermann et al. |
| 5,683,392 A | 11/1997 | Richelsoph et al. |
| 5,690,630 A | 11/1997 | Errico et al. |
| 5,725,527 A | 3/1998 | Biedermann et al. |
| 5,728,098 A | 3/1998 | Sherman et al. |
| 5,733,286 A | 3/1998 | Errico et al. |
| 5,782,833 A | 7/1998 | Haider |
| 5,873,878 A * | 2/1999 | Harms ............... A61B 17/7032 606/308 |
| 5,876,459 A | 3/1999 | Powell |
| 5,879,350 A | 3/1999 | Sherman et al. |
| 5,885,286 A | 3/1999 | Sherman et al. |
| 5,964,760 A | 10/1999 | Richelsoph et al. |
| 6,010,503 A | 1/2000 | Richelsoph et al. |
| 6,050,997 A | 4/2000 | Mullane et al. |
| 6,053,917 A | 4/2000 | Sherman et al. |
| 6,090,111 A | 7/2000 | Nichols |
| 6,162,234 A | 12/2000 | Freedland et al. |
| 6,273,888 B1 | 8/2001 | Justis |
| 6,302,882 B1 | 10/2001 | Lin et al. |
| 6,331,179 B1 | 12/2001 | Freid et al. |
| 6,355,040 B1 * | 3/2002 | Richelsoph ........ A61B 17/7032 606/272 |
| 6,371,957 B1 | 4/2002 | Amrein et al. |
| 6,440,137 B1 * | 8/2002 | Horvath ............ A61B 17/7037 606/302 |
| 6,451,021 B1 | 9/2002 | Ralph et al. |
| 6,457,789 B2 | 10/2002 | Hallsten |
| 6,485,492 B1 | 11/2002 | Halm et al. |
| 6,485,494 B1 | 11/2002 | Haider |
| 6,547,789 B1 | 4/2003 | Ventre et al. |
| 6,554,834 B1 | 4/2003 | Crozet et al. |
| 6,565,565 B1 | 5/2003 | Yuan et al. |
| 6,613,050 B1 * | 9/2003 | Wagner ............ A61B 17/7037 606/250 |
| 6,626,908 B2 | 9/2003 | Cooper et al. |
| 6,755,829 B1 | 6/2004 | Bono et al. |
| 7,087,057 B2 | 8/2006 | Konieczynski et al. |
| 7,141,051 B2 | 11/2006 | Janowski et al. |
| 7,335,201 B2 | 2/2008 | Doubler et al. |
| 7,901,436 B2 | 3/2011 | Baccelli |
| 8,882,808 B2 | 11/2014 | Baccelli |
| 2001/0001119 A1 | 5/2001 | Lombardo |
| 2001/0053913 A1 | 12/2001 | Freedland |
| 2002/0052603 A1 | 5/2002 | Nichols et al. |
| 2002/0082602 A1 | 6/2002 | Biedermann et al. |
| 2002/0133154 A1 | 9/2002 | Saint Martin |
| 2003/0125742 A1 | 7/2003 | Yuan et al. |
| 2003/0199873 A1 * | 10/2003 | Richelsoph ........ A61B 17/7037 606/278 |
| 2004/0176766 A1 * | 9/2004 | Shluzas ............ A61B 17/7032 606/65 |
| 2004/0186474 A1 | 9/2004 | Matthis et al. |
| 2005/0277927 A1 | 12/2005 | Guenther et al. |
| 2011/0152950 A1 | 6/2011 | Baccelli |

FOREIGN PATENT DOCUMENTS

| | | | |
|---|---|---|---|
| DE | 10256095 A1 | 7/2004 | |
| EP | 536066 A1 | 4/1996 | |
| EP | 1064885 A1 | 1/2001 | |
| FR | 2151475 A5 | 4/1973 | |
| FR | 2720923 A1 | 12/1995 | |
| FR | 2780269 A1 | 12/1999 | |
| WO | WO-9203100 A1 | 3/1992 | |
| WO | WO-9501132 A1 | 1/1995 | |
| WO | WO-9621396 A1 | 7/1996 | |
| WO | WO 2003068083 * | 2/2003 | ............ A61B 17/70 |
| WO | 03058086 A2 | 7/2003 | |
| WO | WO-03068086 A1 | 8/2003 | |
| WO | 2004103194 A1 | 12/2004 | |
| WO | WO-2005023126 A1 | 3/2005 | |
| WO | 2005122930 A2 | 12/2005 | |
| WO | WO-2005122930 A2 | 12/2005 | |

OTHER PUBLICATIONS

"U.S. Appl. No. 10/569,607, Final Office Action dated Feb. 26, 2008", 5 pgs.

"U.S. Appl. No. 10/569,607, Final Office Action dated Apr. 27, 2010", 27 pgs.

"U.S. Appl. No. 10/569,607, Final Office Action dated Jun. 1, 2009", 6 pgs.

"U.S. Appl. No. 10/569,607, Non Final Office Action dated Jul. 17, 2007", 6 pgs.

"U.S. Appl. No. 10/569,607, Non Final Office Action dated Nov. 14, 2008", 6 pgs.

"U.S. Appl. No. 10/569,607, Non Final Office Action dated Nov. 25, 2009", 8 pgs.

"U.S. Appl. No. 10/569,607, Notice of Allowance dated Nov. 23, 2010", 4 pgs.

"U.S. Appl. No. 10/569,607, Preliminary Amendment filed Feb. 24, 2006", 3 pgs.

"U.S. Appl. No. 10/569,607, Response filed Feb. 13, 2009 to Non Final Office Action dated Nov. 14, 2008", 8 pgs.

"U.S. Appl. No. 10/569,607, Response filed Feb. 22, 2010 to Non Final Office Action dated Nov. 25, 2009", 9 pgs.

"U.S. Appl. No. 10/569,607, Response filed Jul. 20, 2010 to Final Office Action dated Apr. 27, 2010", 9 pgs.

"U.S. Appl. No. 10/569,607, Response filed Aug. 26, 2008 to Final Office Action dated Feb. 26, 2008", 9 pgs.

"U.S. Appl. No. 10/569,607, Response filed Sep. 1, 2009 to Final Office Action dated Jun. 1, 2009", 9 pgs.

"U.S. Appl. No. 10/569,607, Response filed Nov. 16, 2007 to Non Final Office Action dated Jul. 17, 2007", 8 pgs.

"European Application Serial No. 04787304.7, Examination Notification Art. 94(3) dated Feb. 2, 2009", 4 pgs.

"International Application Serial No. PCT/FR2004/002249, International Preliminary Report on Patentability dated Mar. 6, 2006", 6 pgs.

"International Application Serial No. PCT/FR2004/002249, International Preliminary Report on Patentability dated Jul. 10, 2006", With English translation, 7 pgs.

"International Application Serial No. PCT/FR2004/002249, International Search Report dated Feb. 18, 2005", 3 pgs.

"International Application Serial No. PCT/FR2004/002249; Written Opinion dated Feb. 18, 2005", 11 pgs.

"International Application Serial No. PCT/US2005/020886, International Preliminary Report on Patentability dated Dec. 14, 2006", 15 pgs.

"International Application Serial No. PCT/US2005/020886, International Search Report dated Feb. 22, 2006", 6 pgs.

"International Application Serial No. PCT/US2005/020886, Written Opinion dated Feb. 22, 2006", 14 pgs.

Strong, Simple and Low Profile, Ovation Polyacial System, by Osteotech, Inc., Eatontown, NJ, 6 pages, www.osteotech.com.

(56) References Cited

OTHER PUBLICATIONS

Paragon Posterior Spinal System, Dank Medical, Inc. catalog, Memphis, TN, 1993, 5 pages.
Spiral Radius 90D System Overview. Surgical Dynamics Inc. catalog, Feb. 26, 2001, 10 pages.
Ovtion Polyaxial System, Osteotech, Inc., online catalog, 2003 at www.osteotech.com, printed Jan. 2003, 16 pages.

\* cited by examiner

SPINAL IMPLANT

CROSS-REFERENCE TO RELATED APPLICATIONS

This application is a continuation of U.S. patent application Ser. No. 13/040,404, filed Mar. 4, 2011, which is a continuation of U.S. patent application Ser. No. 10/569,607, filed Nov. 3, 2006, now U.S. Pat. No. 7,901,436, which is a national phase filing of PCT Application No. PCT/FR2004/002249, filed Sep. 3, 2004, which claims priority to French Patent Application No. 0310480, filed Sep. 4, 2003, all of which are incorporated by reference herein.

TECHNICAL FIELD

The invention relates to an implant for spinal surgery and, more particularly, it relates to devices for osteosynthesis and for arthrodesis.

SUMMARY

In the invention, the spinal implant comprises, at a first end, fastener means for fastening to a vertebra, and at a second end, an assembly head extending along an axis x-x', said head including a housing that is open away from the fastener means and that presents a section that is substantially U-shaped, said head being suitable for receiving a connection rod extending transversely to the axis x-x' and for securing it by clip retention means and by locking means.

Such an implant is already known, e.g. from document FR 2 780 269. It relates to a spinal implant of the above-specified type having clip retention means in the form of a protuberance situated in the housing and extending towards the inside thereof. In order to be retained, the connection rod is clipped into the bottom portion of the housing by using the protuberance.

Thereafter, the rod is locked by an external ring that is screwed onto the assembly head. The function of the external ring is to clamp together the side branches of the assembly head, or at least to ensure that they do not splay apart. To do this, the inside diameter of the ring is substantially equal to the outside diameter of the assembly head, so as to be capable of sliding on the assembly head and thus of pressing closely against its side branches.

That outer ring is essential for ensuring that the rod is locked in place. Without that ring, the branches could splay apart because of the force applied to insert the rod in the clip retention means, in particular after the implant has been used on numerous occasions. As a result, the rod would be no longer held sufficiently securely in the housing and could therefore separate from the implant.

The use of an outer ring for the locking means considerably increases the overall dimensions of the implant and obliges the surgeon carrying out the surgery to provide sufficient space in advance around the implant in order to allow the external ring to be put into place.

Another drawback appears when putting the outer ring into place, and more generally when putting any element into place that is to be screwed onto the outside surface of the assembly head of such an implant.

During this locking operation when using an outer ring, it is possible that tissue, veins or nerves, can become entrained by the turning ring or can be pinched between the ring and the assembly head. In addition, in the mounted position, the external parts or threads present sharp edges that could cut through tissue situated close to the implant. It will readily be understood that it is desirable, whenever possible, to avoid damaging human tissue.

Another drawback of previously known implants lies in the fact that the surgeon must constantly hold the rod in place while its position is being adjusted, or indeed until the assembly head has been locked.

The invention seeks to remedy those drawbacks.

This object is achieved by the facts that, in the assembled position, the clip retention means and the locking means are fully received within the assembly head, and that the clip retention means (40) are mechanically decoupled from the locking means (50).

The term "clip retention means" designates means serving to prevent the rod becoming disassembled easily, while still leaving it free to turn about its own axis and to move in translation lengthwise.

The term "locking means" is used to designate means that prevent any movement of the rod relative to the assembly head.

The clip retention means are suitable for holding the connection rod in the assembly head on their own; in other words, the retention means can perform their function in the absence of the locking means, or even before the assembly head is locked.

It will be understood that that spares the surgeon of any need to hold the connection rod while adjusting the position of the implant or of the rod, and/or while locking the assembly head.

In addition, all of the means required for securing the connection rod are contained within the assembly head. No element is screwed or inserted on the outside surface of the assembly head, so there is no risk of damaging tissue or veins in the vicinity of the implant.

Advantageously, the clip retention means are constituted by a part that is separate and that can be separated from the assembly head.

Thus, it is possible to change the clip retention means so as to adapt to the diameter of the connection rod that is to be used. This change could also be necessary if, after several uses, the clip retention means no longer perform their function.

Advantageously, the locking means comprise a locknut suitable for being screwed into internal tapping of the assembly head.

Thus, in the assembled position, the locknut is received in full inside the assembly head.

BRIEF DESCRIPTION OF THE DRAWINGS

The invention can be better understood and its advantages can be seen better on reading the following detailed description of embodiments given as non-limiting examples. The description refers to the accompanying drawings, in which.

DETAILED DESCRIPTION

Figure 1:
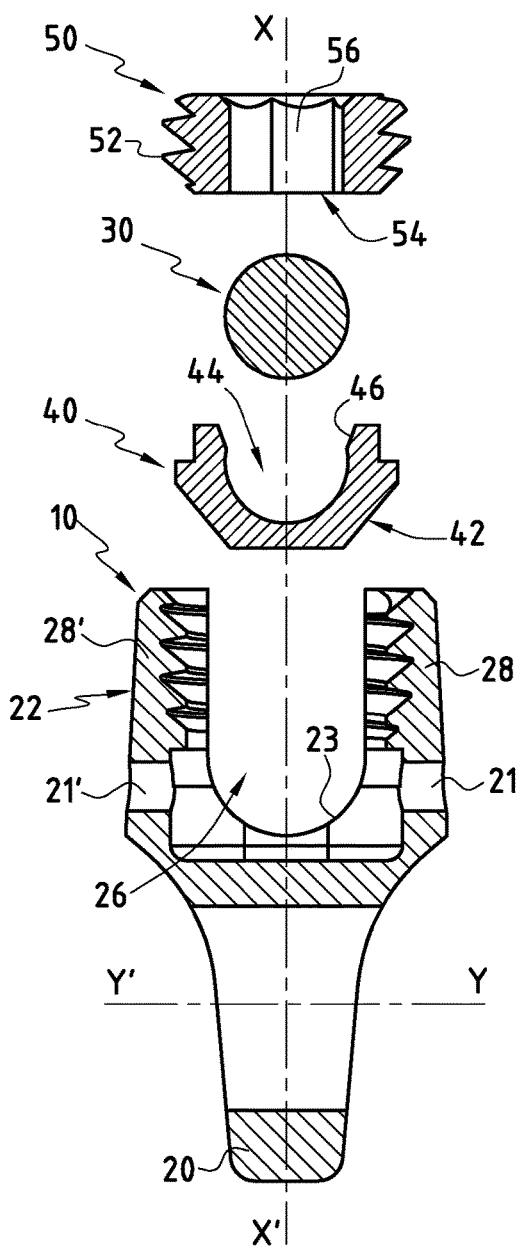
FIG. 1 is a face view in exploded section showing the various components of the spinal implant and the connection rod.

FIG. 1 shows the spinal implant in a face view and in section.

As can be seen in this figure, the spinal implant 10 has, at its first end, fastener means 20 in the form of a hook. The hook is used for securing the spinal implant to a process of a vertebra (not shown herein).

The second end of the implant comprises an assembly head 22 suitable for securing connection rods 30. Such rods serve to correct the orientation of the spinal column of a patient suffering from scoliosis, for example.

The implant shown herein has transverse and longitudinal dimensions lying in the range 5 millimeters (mm) to 20 mm. The connection rod 30 may have a variety of diameters, preferably lying in the range 5 mm to 6 mm.

The assembly head 22 of the spinal implant presents an outside shape that is substantially cylindrical about the axis x-x'. It possesses internal tapping 24 and has two side openings 26, 26' which between them define two side walls 28, 28'.

As can be seen in FIG. 1, the section of the assembly head in a plane (XOY) orthogonal to the plane of symmetry of the implant, is substantially U-shaped, and the bottom portions of the openings present semicylindrical profiles 23 for supporting the outside surface of the connection rod 30.

The internal tapping 24 of the assembly head 22 is of the "artillery" type, i.e. it presents an asymmetric trapezoidal thread. The advantage of this type of thread is that it enables the radial component of the screw-fastening force to be reduced. The advantage of this is explained in greater detail below.

The assembly head 22 further includes two orifices 21, 21' situated in the side walls 28, 28'. During the surgical operation, the surgeon uses an instrument for putting the implant into place. At one of its ends, the instrument has two studs that are received in the orifices 21, 21' in order to hold the implant.

Once the surgeon has determined the type of connection rod 30 that is to be used, clip retention means 40 are placed in the assembly head 22 to retain the connection rod in the assembly head before it is locked. The known advantage is to avoid any need for the surgeon to hold the connection rod while adjusting the position of the rod and while locking it. While position is being adjusted, the rod can move in translation in the retention means 40 and can also pivot about its own axis. However, the retention means 40 prevents the rod from escaping from the assembly head 22.

The retention means is in the form of a clip insert 40. Several types of inserts are available corresponding to rods 30 of different diameters.

All these various inserts can be fitted in the same assembly head 22.

The insert is in the form of a cylindrical part of diameter slightly smaller than the inside diameter of the opening in the assembly head, and on its bottom portion it carries a thread 42 to enable it to be secured to the head by being turned through one-fourth of a turn.

In its top portion, it presents an open cylindrical opening 44 of diameter substantially equal to the diameter of the connection rod, and extending over slightly less than 180° so as to cover the connection rod in part when it is engaged in the insert. It will be understood that this engagement is achieved by applying a small amount of force on the connection rod so as to deform the top 46 of its cap-shape temporarily. This forced engagement clips the connection rod into the insert 40.

Once the rod 30 is properly in position, the surgeon can proceed to lock it in position.

Figure 2:
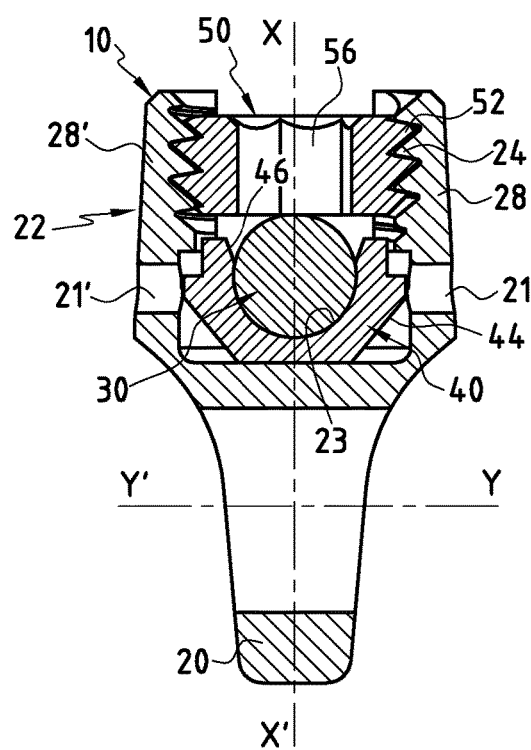
FIG. 2 is a face view in section, in the assembled position, showing the spinal implant and the connection rod.
Figure 3:
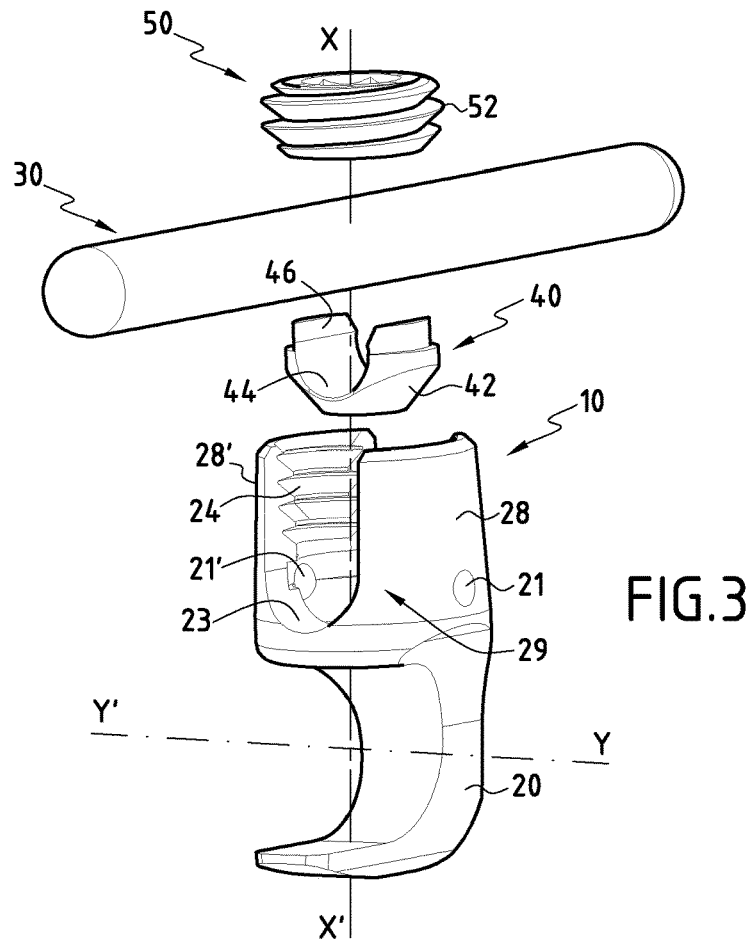
FIG. 3 is an exploded view in perspective showing the various components of the spinal implant and of the connection rod.

The locking means have inside tapping 24 as mentioned above and a locknut 50 that is to be screwed into the tapping 24. As can be seen in FIGS. 1 and 2, the locknut is cylindrical in shape and possesses an "artillery" type thread 52 suitable for co-operating with the tapping 24 of the assembly head 22.

When the locknut 50 is screwed into the assembly head 22, its bottom portion 54 comes into contact with the outside surface of the rod so as to secure the rod to the implant. The top portion of the locknut includes, in conventional manner, a hexagonal socket 56 suitable for receiving a tightening tool (not shown herein).

The use of a thread of the "artillery" type presents the advantage of reducing radial force while tightening the locknut. As a result, the side walls 28, 28' are no longer subjected to a radial force tending to splay them apart from each other.

By using this type of tapping, there is no longer any need to use an external hooping ring for holding the walls at the desired spacing.

In any event, even if there is any residual force tending to space the walls 28, 28' apart, the insert 40 would continue to hold the rod 30, since the insert and the assembly head are mechanically decoupled, i.e. the mechanical forces to which the assembly head 22 is subjected are not transmitted to the insert 40.

It will thus be understood that it is entirely pointless using an external hooping ring with this device.

Figure 4:
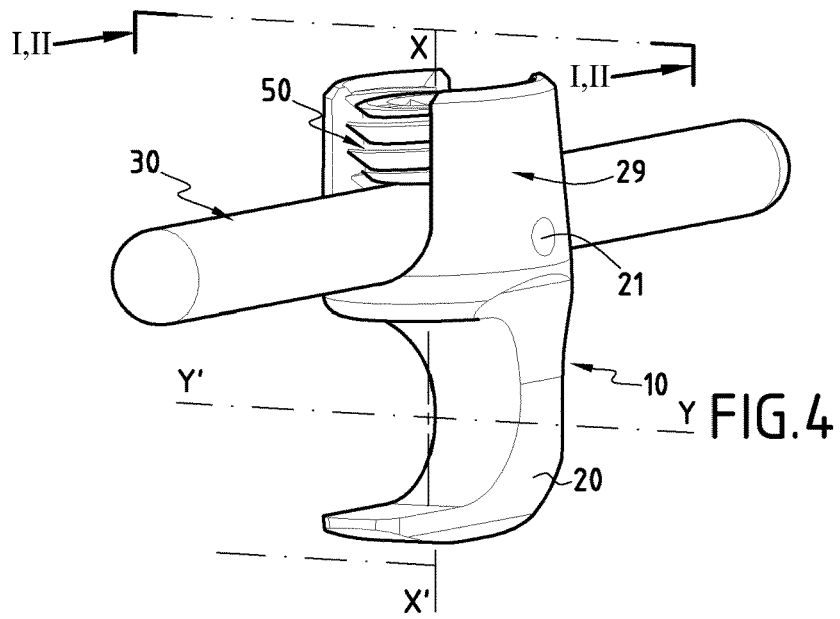
FIG. 4 is a perspective view of the implant in the assembled position together with the connection rod.
Figure 5:
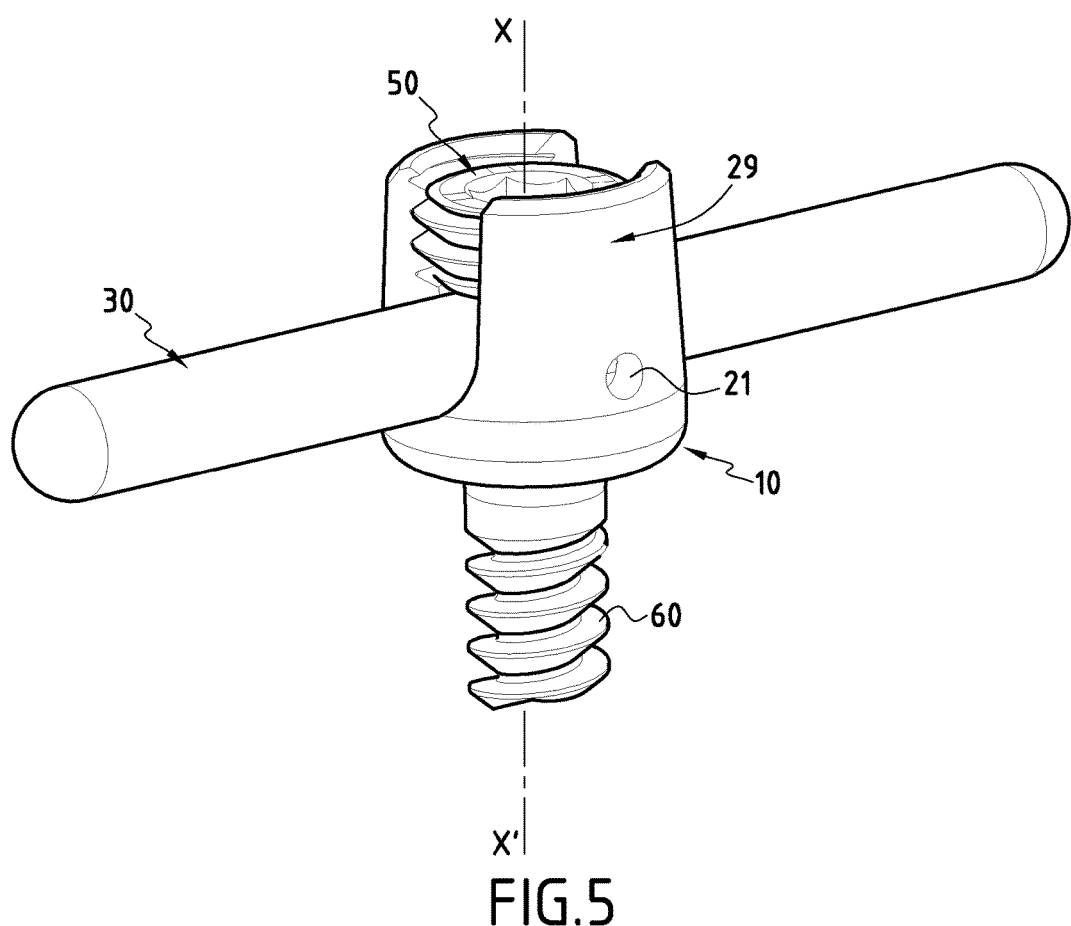
FIG. 5 is a perspective view of another variant of the spinal implant.

Another advantage is explained below:

In the locked position, as can be seen in FIGS. 4 and 5, the locknut 50 is fully received inside the assembly head 22 so the outside profile 29 of the implant is smooth; in other words, it does not present any tapping, bulges, grooves, or roughness that might damage the surrounding tissue.

On the same lines, there are no additional parts on the outside surface of the assembly head, for example hooping rings, that might present sharp edges that could damage surrounding tissue.

In other variants, the implant may present smooth surfaces 29 of other shapes, of the "smooth profile" type, that can be inserted reliably in the human body without any risk of provoking internal lesions.

Without going beyond the invention, the implant can thus present a profile presenting a surface that is circularly symmetrical with a characteristic meridian in the form of a curve that is continuous and continuously differentiable. In other words, there is no point of inflection or reversal, thereby ensuring that the profile is smooth.

In another variant of the invention, as shown in FIG. 5, the fastener means comprise a screw 60 for anchoring in a vertebra.

What is claimed is:

1. A spinal implant, comprising:
   a spinal rod comprising a circumference;
   a clip insert adapted to receive and retain the spinal rod within a partial cylindrical transverse opening in a proximal portion of the clip insert while allowing rotation and translation of the rod relative to the clip insert when the spinal rod is within the partial cylindrical transverse opening, wherein the proximal portion of the clip insert is temporarily deformable by application of force on the spinal rod to engage the spinal rod with the clip insert, wherein the clip insert is in the form of a cylindrical body before and after temporarily deforming to engage the spinal rod;

an assembly head comprising a distal first end adapted to engage and secure the assembly head to a vertebra and a proximal second end comprising two opposed sidewalls which define an axial cylindrical threaded cavity for receiving the cylindrical body of the clip insert and extending from the proximal second end at least partially toward the distal first end and which additionally define two U-shaped channels open in an axial direction toward the proximal second end of the assembly head and closed in a direction toward the distal first end of the assembly head and adapted to receive the spinal rod in a transverse orientation relative to an axis of the axial cylindrical threaded cavity, wherein the assembly head is adapted to retain the clip insert therein via an external thread included on a distal portion of the insert that permits the clip insert to be inserted into the assembly head with the external thread aligned with the two U-shaped channels and then rotated one-fourth of a turn within the axial cylindrical threaded cavity of the assembly head to align the partial cylindrical transverse opening with the two-U-shaped openings and engage the external thread with an arcuate groove in the assembly head to secure the insert to the assembly head; and a locking member comprising distal and proximal ends and an externally threaded portion adapted to threadably engage the threaded cavity, wherein when the externally threaded portion of the locking member is engaged with the threaded cavity, the locking member is adapted to force the spinal rod against a base portion of the two U-shaped channels thereby preventing translational and rotational motion of the spinal rod relative to the assembly head, wherein threaded engagement of the externally threaded portion of the locking member with the axial cylindrical threaded cavity of the assembly head does not transmit direct compressive forces to the clip insert, and wherein at least a portion of the spinal rod separates the locking member from the clip insert when the spinal rod is retained within the partial cylindrical transverse opening of the clip insert.

2. The spinal implant according to claim 1, wherein when the threaded portion of the locking member is engaged with the threaded cavity to force the spinal rod against the base portion of the U-shaped channels, the proximal end of the locking member is fully received within the two opposed walls of the assembly head.

3. The spinal implant according to claim 1, wherein the proximal portion of the clip insert extends partially around the circumference of the spinal rod.

4. The spinal implant according to claim 3, wherein the proximal portion of the clip insert which extends partially around the circumference of the spinal rod subtends a circumferential arc of more than 180 degrees, wherein the clip insert contacts the rod along the circumferential arc.

5. The spinal implant according to claim 4, wherein the proximal portion of the clip insert which extends partially around the circumference of the spinal rod does not contact the locking member when the locking member is engaged with the threaded cavity.

6. The spinal implant according to claim 1, wherein the clip insert is adapted to be retained within the assembly head when the locking member is not engaged with the threaded cavity.

7. The spinal implant according to claim 1, wherein the clip insert is adapted to retain the spinal rod within the assembly head when the locking member is not engaged with the threaded cavity.

8. The spinal implant according to claim 1, wherein the distal first end of the assembly head adapted to engage and secure the assembly head to a vertebra comprises a hook adapted to connect the assembly head to a pedicle of a vertebra.

9. The spinal implant according to claim 1, wherein the distal first end of the assembly head adapted to engage and secure the assembly head to a vertebra comprises a screw adapted to anchor the assembly head in a vertebra.

10. The spinal implant according to claim 1, wherein the clip insert is insertable into the threaded cavity along the axial direction.

* * * * *